United States Patent
Nantermet et al.

(10) Patent No.: US 7,816,378 B2
(45) Date of Patent: Oct. 19, 2010

(54) CYCLIC KETAL BETA-SECRETASE INHIBITORS FOR THE TREATMENT OF ALZHEIMER'S DISEASE

(75) Inventors: Philippe G. Nantermet, Lansdale, PA (US); Joseph P. Vacca, Telford, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 322 days.

(21) Appl. No.: 11/989,990

(22) PCT Filed: Jul. 28, 2006

(86) PCT No.: PCT/US2006/029766
§ 371 (c)(1),
(2), (4) Date: Feb. 1, 2008

(87) PCT Pub. No.: WO2007/019111
PCT Pub. Date: Feb. 15, 2007

(65) Prior Publication Data
US 2009/0176836 A1   Jul. 9, 2009

Related U.S. Application Data

(60) Provisional application No. 60/705,075, filed on Aug. 3, 2005.

(51) Int. Cl.
- A61K 31/44 (2006.01)
- A61K 31/34 (2006.01)
- C07D 405/00 (2006.01)
- C07D 307/02 (2006.01)
- A01N 43/36 (2006.01)

(52) U.S. Cl. ............ 514/336; 546/283.4; 514/422; 514/473; 548/517; 549/475

(58) Field of Classification Search ........ 546/284.7; 514/461; 549/480
See application file for complete search history.

(56) References Cited

U.S. PATENT DOCUMENTS

| | | | |
|---|---|---|---|
| 7,109,217 B2 | 9/2006 | Coburn et al. | |
| 7,115,652 B2 | 10/2006 | Yang | |
| 7,132,568 B2 | 11/2006 | Yang et al. | |
| 7,291,620 B2 | 11/2007 | Coburn et al. | |
| 2001/0016595 A1 | 8/2001 | Ducharme et al. | |
| 2006/0149092 A1 | 7/2006 | Nantermet et al. | |
| 2006/0293380 A1 | 12/2006 | Nantermet et al. | |
| 2007/0088165 A1 | 4/2007 | Nantermet et al. | |
| 2007/0142634 A1 | 6/2007 | Barrow et al. | |

FOREIGN PATENT DOCUMENTS

| | | |
|---|---|---|
| WO | WO 2005/051914 | 6/2005 |
| WO | WO 2005/051914 A1 | 6/2005 |
| WO | WO 2005/065195 | 7/2005 |
| WO | WO 2005/065195 A2 | 7/2005 |

OTHER PUBLICATIONS

Luethy et. al., "Preparation of substituted pyridines as herbicides", Hcaplus 2005:564642 abstract, Jun. 30, 2005.*

* cited by examiner

*Primary Examiner*—Janet L Andres
*Assistant Examiner*—Binta M Robinson
(74) *Attorney, Agent, or Firm*—Keith D. MacMillan; John C. Todaro

(57) ABSTRACT

The present invention is directed to cyclic ketal compounds of formula (I)

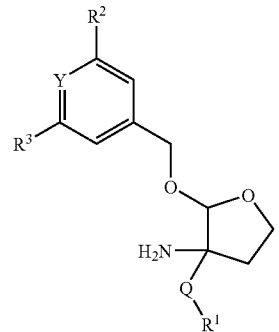

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

17 Claims, No Drawings

CYCLIC KETAL BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) of U.S. Provisional Application Ser. No. 60/705,075, filed Aug. 3, 2005.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to cyclic ketal compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to cyclic ketal compounds represented by general formula (I)

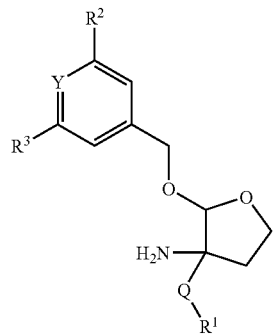

and individual enantiomers and diastereoisomers thereof, and pharmaceutically acceptable salts thereof, which are useful as inhibitors of the β-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to cyclic ketal compounds represented by general formula (I)

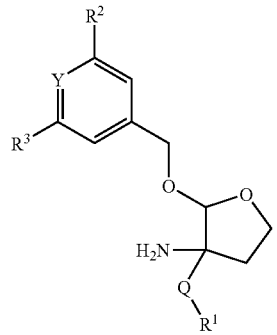

wherein

Y is N or CH;

Q is —$C_{0-3}$ alkylene, wherein said alkylene is unsubstituted or substituted with one or more
 (1) halo,
 (2) —$C_{3-12}$ cycloalkyl,
 (3) —OH,
 (4) —CN, (5) —O—$C_{1-10}$ alkyl, and
(6) —$C_{1-10}$ alkyl;

$R^1$ is (1) aryl selected from the group consisting of phenyl and napthyl,
(2) heteroaryl,
(3) —$C_{1-10}$ alkyl, and
(4) —$C_{3-8}$ cycloalkyl, said cycloalkyl optionally fused to a $C_{6-10}$ aryl group,
wherein said alkyl, cycloalkyl, aryl or heteroaryl is unsubstituted or substituted with one or more
(a) halo,
(b) —$C_{1-10}$ alkyl, wherein said alkyl is unsubstituted or substituted with halogen,
(c) —H,
(d) —CN,
(e) —O—$C_{1-10}$ alkyl,
(f) —$C_{3-12}$ cycloalkyl, and
(g) —$NR^{12}R^{13}$, wherein $R^{12}$ and $R^{13}$ are selected from the group consisting of
(i) hydrogen,
(ii) —$C_{1-10}$ alkyl, and
(iii) —$C_{0-6}$ alkyl-$C_{6-10}$ aryl;

$R^2$ is selected from the group consisting of:
(1) ($R^4$—$SO_2$)N($R^7$)—, wherein $R^4$ is
(a) —$C_{1-10}$ alkyl,
(b) —$C_{2-10}$ alkenyl,
(c) —$C_{2-10}$ alkynyl, or
(d) —$C_{3-8}$ cycloalkyl,
wherein said alkyl, alkenyl, alkynyl and cycloalkyl is unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(Vii) —$C_{2-10}$ alkynyl,
(viii) —$C_{3-8}$ cycloalkyl,
(ix) aryl selected from the group consisting of phenyl and napthyl, or
(x) heteroaryl,
and said aryl and heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{1-10}$ alkyl,
(vii) —$C_{2-10}$ alkenyl, or
(viii) $C_{2-10}$ alkynyl;

$R^7$ is selected from the group consisting of
(a) hydrogen,
(b) $C_{1-10}$ alkyl,
(c) —$C_{2-10}$ alkenyl, or
(d) —$C_{2-10}$ alkynyl,
wherein said alkyl, alkenyl or alkynyl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) aryl selected from the group consisting of phenyl and napthyl, or
(vii) heteroaryl,
and said cycloalkyl, aryl or heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl, or
(vi) aryl selected from the group consisting of phenyl and napthyl;

(2)

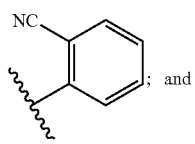
; and (3)

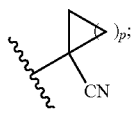

$R^3$ is selected from the group consisting of

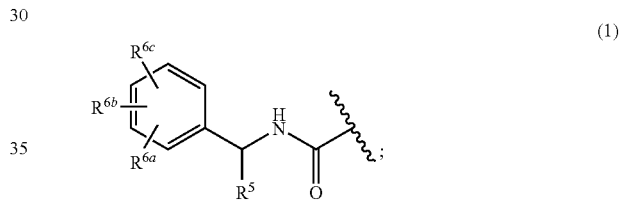

wherein $R^5$ is selected from the group consisting of
(1) —$C_{1-10}$ alkyl,
(2) —$C_{2-10}$ alkenyl, or
(3) —$C_{2-10}$ alkynyl,
wherein said alkyl, alkenyl or alkynyl is unsubstituted or is substituted with one or more halo;

$R^{6a}$, $R^{6b}$, and $R^{6c}$ are independently selected from the group consisting of:
(1) hydrogen,
(2) halo,
(3) —$C_{1-10}$ alkyl,
(4) —$C_{2-10}$ alkenyl,
(5) —$C_{2-10}$ alkynyl,
(6) —H,
(7) —OH,
(8) —$C_{3-8}$ cycloalkyl, and
(9) —O—$C_{1-10}$ alkyl;

$R^9$ and $R^{10}$ are independently selected from the group consisting of
- (1) hydrogen,
- (2) —$C_{1-10}$ alkyl,
- (3) —$C_{2-10}$ alkenyl,
- (4) —$C_{2-10}$ alkynyl, or
- (5) —$C_{3-8}$ cycloalkyl,
- wherein said alkyl, alkenyl, alkynyl or cycloalkyl is unsubstituted or substituted with one or more
  - (a) halo,
  - (b) —OH,
  - (c) —CN,
  - (d) —$C_{3-8}$ cycloalkyl, or
  - (e) —O—$C_{1-10}$ alkyl or $R^9$ and $R^{10}$ are joined together with the nitrogen atom to which they are attached to form a pyrrolidine ring, which is unsubstituted or substituted with one or more
- (a) $C_{1-10}$ alkyl,
- (b) —$C_{2-10}$ alkenyl,
- (c) —$C_{2-10}$ alkynyl,
- (d) —$C_{3-8}$ cycloalkyl,
- (e) —$(CH_2)_n$-phenyl,
- (f) —CN,
- wherein said alkyl, alkenyl or alkynyl is unsubstituted or substituted with one or more
  - (i) halo,
  - (ii) —OH,
  - (iii) —CN.
  - (iv) —O—$C_{1-10}$ alkyl, or
  - (v) —$C_{3-8}$ cycloalkyl,
- and said cycloalkyl and phenyl is unsubstituted or substituted with one or more
  - (i) halo,
  - (ii) —$C_{1-10}$ alkyl,
  - (iii) —$C_{2-10}$ alkenyl,
  - (iv) —$C_{2-10}$ alkynyl,
  - (v) —OH,
  - (vi) —CN,
  - (vii) —$C_{3-8}$ cycloalkyl, or
  - (viii) —O—$C_{1-10}$ alkyl;

$R^8$ is selected from the group consisting of
- (1) hydrogen,
- (2) —$C_{1-10}$ alkyl,
- (3) —$C_{2-10}$ alkenyl,
- (4) —$C_{2-10}$ alkynyl, or
- (5) —$CH_2$— phenyl,
- wherein said alkyl, alkenyl, alkynyl or phenyl is unsubstituted or substituted with one or more
  - (a) halo,
  - (b) —OH,
  - (c) —CN,
  - (d) —$C_{3-8}$ cycloalkyl, and
  - (e) —O—$C_{1-10}$ alkyl;

$R^{12}$ is selected from the group consisting of
- (1) hydrogen,
- (2) —$C_{1-10}$ alkyl,
- (3) —$C_{2-10}$ alkenyl,
- (4) —$C_{2-10}$ alkynyl,
- (5) halo,
- (6) —$C_{3-8}$ cycloalkyl,
- (7) aryl selected from the group consisting of phenyl and napthyl, and
- (8) heteroaryl,
- wherein said aryl and heteroaryl is unsubstituted or substituted with one or more
  - (a) halo,
  - (b) —OH,
  - (c) —CN,
  - (d) —O—$C_{1-10}$ alkyl,
  - (e) —$C_{3-8}$ cycloalkyl,
  - (f) —$C_{1-10}$ alkyl,
  - (g) —$C_{2-10}$ alkenyl, or
  - (h) —$C_{2-10}$ alkynyl n is 0, 1, 2, 3 or 4;

p is 1, 2, 3 or 4;

and pharmaceutically acceptable salts thereof, and individual enantiomers and diastereomers thereof.

In one embodiment, the invention is directed to compounds of formula (I) wherein $R^1$ is phenyl, unsubstituted or substituted, and Q is preferably $CH_2$. Preferably, $R^1$ is unsubstituted phenyl or 4-fluorophenyl.

In other embodiments, $R^1$ is heteroaryl. Preferred $R^1$ heteroaryl groups include pyridyl (2-pyridyl, 3-pyridyl or 4-pyridyl), thienyl (preferably 2-thienyl or 3-thienyl), thiazole and indynyl.

In other embodiments, $R^1$ is $C_{1-12}$ alkyl or a $C_{3-8}$ cycloalkyl group. Preferred $C_{1-12}$ alkyl $R^1$ groups include $C_{1-6}$ alkyl (preferably unsubstituted $C_{1-6}$ alkyl, including methyl and isopropyl.) Preferred $C_{3-8}$ cycloalkyl groups include cyclopropyl, cyclopentyl and cyclohexyl, preferably unsubstituted. Two of the ring carbon atoms from the cycloalkyl group may be linked to form a $C_{6-12}$ aryl. An exemplary fused group of this embodiment is:

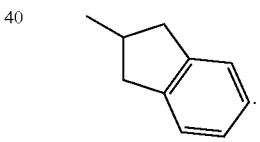

In a preferred embodiment of the compounds of the invention, $R^2$ is selected from the group consisting of
- (1) $(R^4—SO_2)N(R^7)$—, wherein $R^4$ is —$C_{1-6}$ alkyl, wherein said alkyl is unsubstituted or substituted with one or more
  - (i) halo,
  - (ii) —OH,
  - (iii) —CN,
  - (iv) —O—$C_{1-6}$ alkyl, or
  - (v) —$C_{1-6}$ alkyl,
- $R^7$ is selected from the group consisting of
  - (a) hydrogen,
  - (b) —$C_{1-6}$ alkyl,
    - wherein said alkyl is unsubstituted or substituted with one or more
      - (i) halo,
      - (ii) —OH, (iii) —CN,
(iv) —O—C$_{1-6}$ alkyl,
(v) —C$_{1-6}$ alkyl, (2)

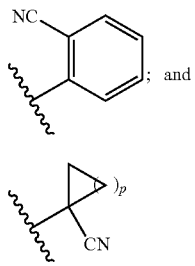
; and (3)

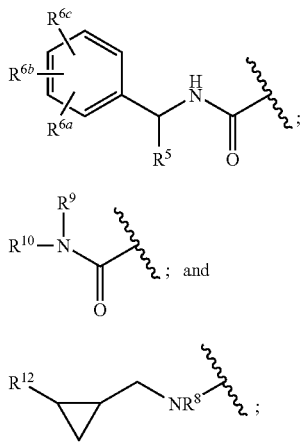

In a preferred embodiment of the compounds of the invention, R$^3$ is selected from the group consisting of (a)

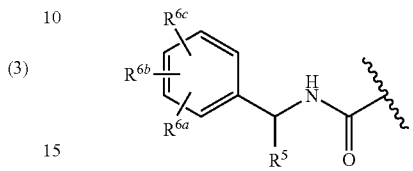
;

(b)

R$^{10}$—N(R$^9$)—C(=O)—⁓ ; and (c)

R$^{12}$—[cyclopropyl]—CH$_2$—NR$^8$—⁓ ;

wherein R$^5$ is C$_{1-6}$ alkyl, optionally substituted with one or more halogen (preferably fluoro);

R$^{6a}$, R$^{6b}$, and R$^{6c}$ are independently selected from the group consisting of:
(1) hydrogen,
(2) halo,
(3) —C$_{1-6}$ alkyl,
(4) —OH,
(5) —CN, and
(6) —O—C$_{1-6}$ alkyl;

R$^9$ and R$^{10}$ are independently selected from the group consisting of
(1) hydrogen, and
(2) —C$_{1-6}$ alkyl,
or R$^9$ and R$^{10}$ are joined together with the nitrogen atom to which they are attached to form a pyrrolidine ring, which is unsubstituted or substituted with one or more
(a) C$_{1-6}$ alkyl,
(b) —(CH$_2$)$_n$-phenyl;
wherein said alkyl and phenyl is unsubstituted or substituted with one or more
(i) halo,
(ii) —C$_{1-6}$alkyl,
(iii) —OH,
(iv) —CN, or
(v) —O—C$_{1-6}$ alkyl; and R$^8$ is hydrogen;
R$^{12}$ is selected from the group consisting of
(1) hydrogen,
(2) —C$_{1-6}$ alkyl.

In a more preferred embodiment of the compounds of the invention, R$^3$ is (a)

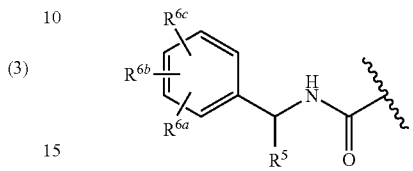

wherein R$^5$, R$^{6a}$, R$^{6b}$, R$^{6c}$ are as defined above. In preferred embodiments, R$^5$ is C$_{1-6}$ alkyl, optionally substituted with one or more halogen (preferably fluoro); and R$^{6a}$, Rb, and R$^{6c}$ are independently selected from the group consisting of:
(1) hydrogen,
(2) halo,
(3) —C$_{1-6}$alkyl,
(4) —OH,
(5) —CN, and
(6) —O—C$_{1-6}$alkyl.

In a more preferred embodiment, R$^3$ is (a) as described above and R$^5$ is methyl. In another preferred embodiment, R$^3$ is (a) as described above and R$^{6a}$ and R$^{6b}$ are hydrogen and R$^{6c}$ is fluoro.

In another embodiment of the compounds of the invention, Y is CH.

In another embodiment of the compounds of the invention, Y is N.

Within the genus of compounds of formula (I), there is a sub-genus of compounds of formula (II)

(II)

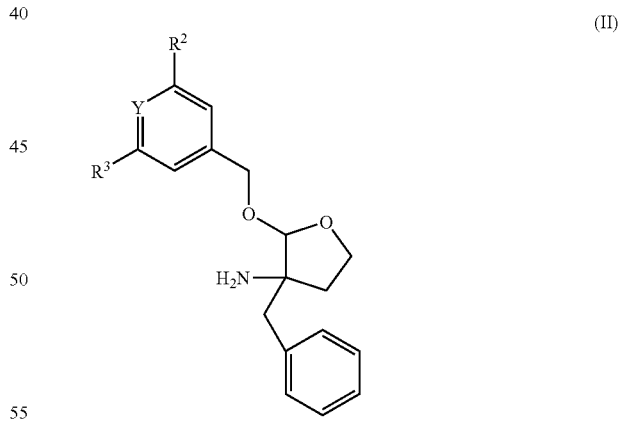

wherein R$^2$, R$^3$ and Y are as described above, and pharmaceutically acceptable salts thereof, and individual enantiomers and diastereomers thereof.

The invention is also directed to methods of treating mammals for diseases in which the 3-secretase enzyme is involved, such as Alzheimer's disease, by administering a therapeutically effective amount of a cyclic ketal compound of formula the invention.

The invention is also directed to pharmaceutical compositions which include an effective amount of a cyclic ketal compound of the invention, or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a cyclic ketal compound of the invention, or a pharmaceutically acceptable salt thereof, with a pharmaceutical carrier or diluent.

The invention is also directed to a method for the manufacture of a medicament or a composition for treating Alzheimer's Disease in humans, comprising combining a cyclic ketal compound of the invention, or a pharmaceutically acceptable salt thereof, with a pharmaceutical carrier or diluent.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "$C_0$ alkyl," for example in the term "—$C_0$alkyl-$C_{6-12}$ aryl", refers to a bond.

As used herein, the term "alkylene," by itself or as part of another substituent, means a saturated straight or branched chain divalent hydrocarbon radical having the number of carbon atoms designated.

The term $C_0$ alkylene means that the alkylene group is absent.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. The preferred single ring aryl group for use in the invention is phenyl. Preferred fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Preferred heteroaryl groups have from 5 to 12 ring atoms. Exemplary heteroaryl groups for use in the invention include benzoxazolyl, triazinyl, furanyl, pyranyl, benzofuranyl, isobenzofuranyl, chromenyl, thienyl, thiophenyl, benzothiophenyl, pyrrolyl, pyrazolyl, imidazolyl, pyridyl, pyrazinyl, pyrimidinyl, pyridazinyl, indolyl, benzimidazolyl, quinolinyl, isoquinolinyl, tetrazolyl, indazolyl, napthyridinyl, triazolyl, oxazolyl, oxadiazolyl, thiazolyl, thiadiazolyl, isoxazolyl, tetrahydroquinolinyl, tetrahydroisoquinolinyl and dihydroindolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

Compounds described herein may contain one or more double bonds, and may thus give rise to cis/trans isomers as well as other conformational isomers. The present invention includes all such possible isomers as well as mixtures of such isomers.

Formula (I) is shown above without a definite stereochemistry at certain positions. The present invention includes all stereoisomers of formula (I), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds claimed in this invention can be prepared according to the following general procedure methods.

In Scheme 1, amine 1 is converted to the corresponding Schiff base which upon treatment with base and alkylating agent is converted to intermediate 2. Interconversion to a Boc protecting group and reduction gives access to hemiketal 4, ready for glycosylation.

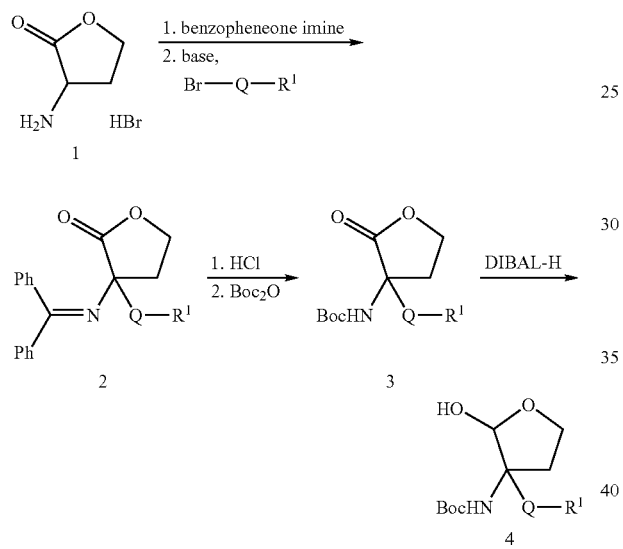

In Scheme 2, aniline 5 is sulfonylated, alkylated and then hydrolysed/reduced to alcohol 6. Alternatively, a bromide can be present (alcohol 8) as a future handle to introduce numerous groups, such as sulfonamides, aryls, etc, on that position via Pd(0) catalysis.

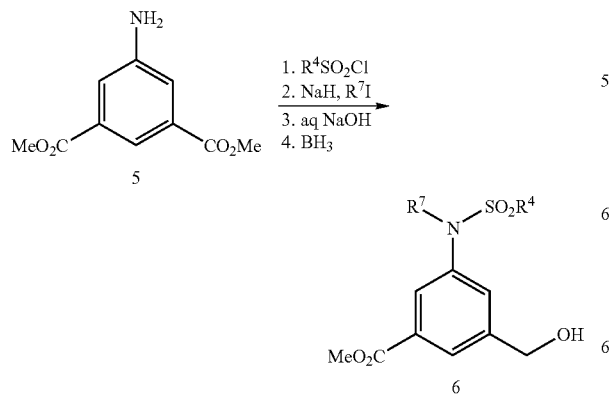

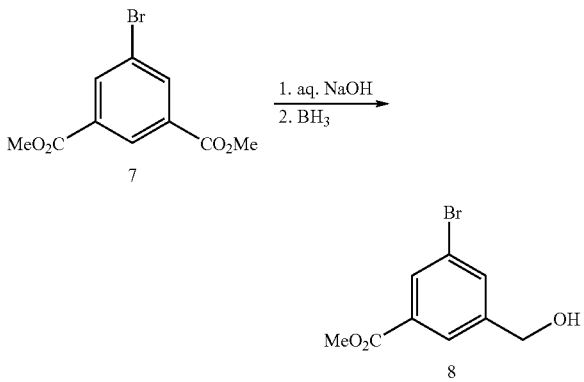

Scheme 3 illustrates the preparation of biaryl alcohols of type 10.

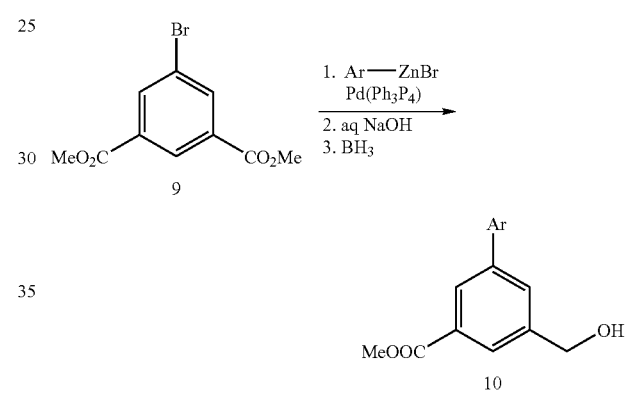

Scheme 4 illustrates the preparation of chloropyridine alcohols of type 12.

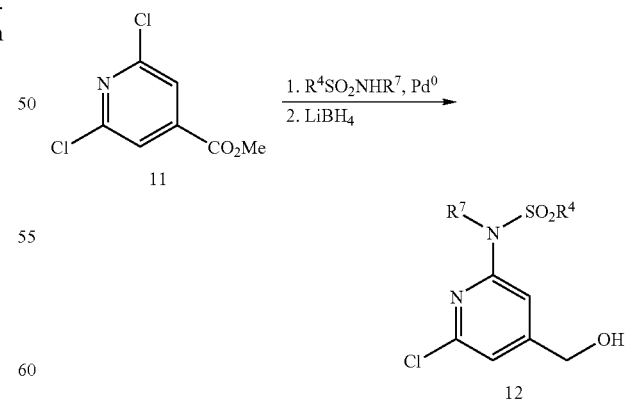

Scheme 5 describes the coupling of hemiketal 4 and alcohol 6, to give ketal of type 13. Hydrolysis of the methyl ester and standard coupling of an amine gives access to structures of type 14.

Scheme 5

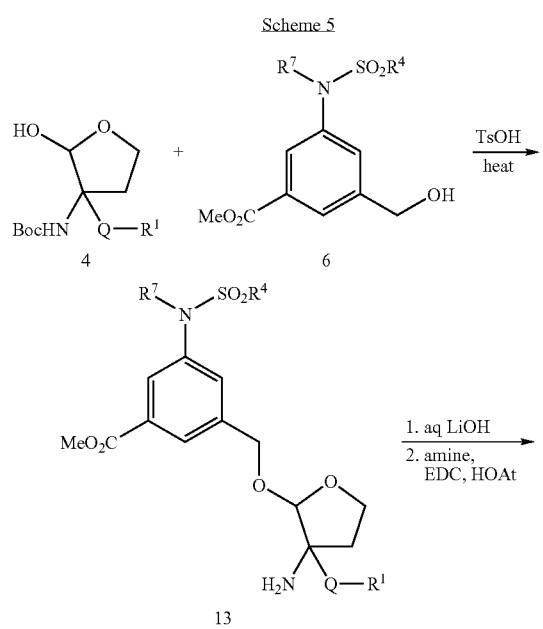

In scheme 6, similar procedures as in scheme 5 allow for the preparation of biaryl ketals of type 16.

Scheme 6

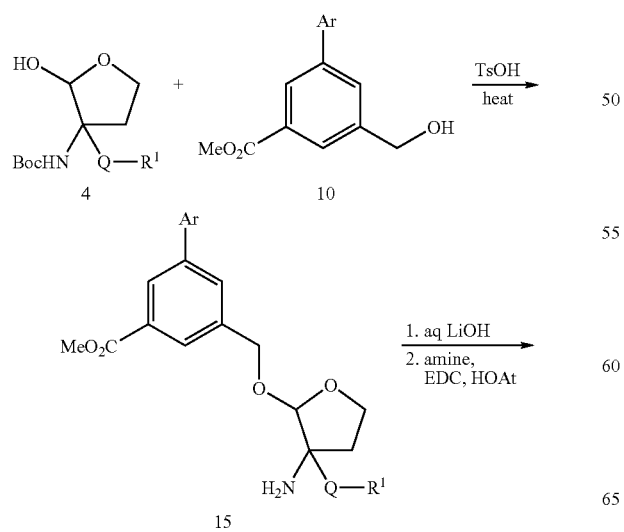

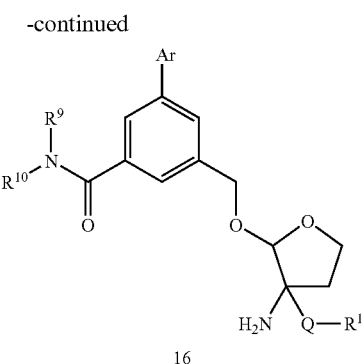

Scheme 7 illustrates the coupling of hemiketal 4 and alcohol 12 to afford ketal 17. Pd(0) mediated amination leads to products of type 18.

Scheme 7

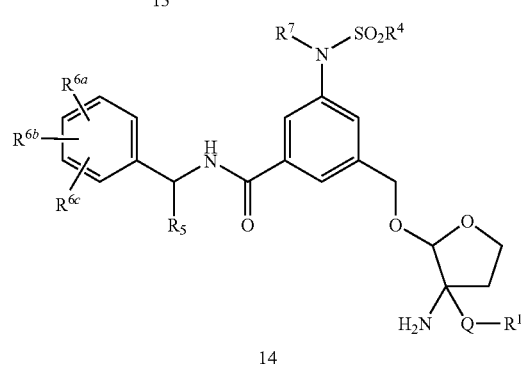

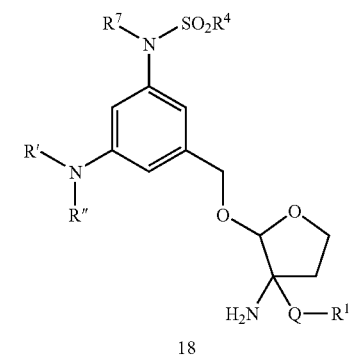

The schemes above may be varied to synthesize additional compounds of formula (I) according to the syntheses described in commonly owned International applications nos. WO 2005/103043, published Nov. 3, 2005, and WO 2005/103020, published Nov. 3, 2005.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the cyclic ketal compounds of the invention disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors; alpha 7 nicotinic agonists, such as SSR 180711, MEM3454 and MEM63908; gamma-secretase inhibitors, such as LY450139, LY411575 and TAK 070; gamma secretase modulators, such as E2012; tau phosphorylation inhibitors; blockers of Aβ oligomer formation; 5-HT4 agonists, such as PRX 03140; 5HT6 antagonists, such as GSK 742457, SGS-518, SAM315, E6795, SL-65.0155, SRA-333 and xaliproden; p25/CDK5 inhibitors; HMG-CoA reductase inhibitors; NK1/NK3 receptor antagonists; NSAID's including ibuprofen; vitamin E; anti-amyloid antibodies (including anti-amyloid humanized monoclonal antibodies), such as bapineuzumab, AAB002, RN1219, ACC001, CAD106 and AZD3102; 5-HT1A antagonists, such as lecozotan; COX-2 inhibitors; anti-inflammatory compounds, such as (R)-flurbiprofen, nitroflurbiprofen, rosiglitazone, ND-1251, VP-025, HT-0712 and EHT-202; CB-1 receptor antagonists or CB-1 receptor inverse agonists, such as AVE 1625; antibiotics such as doxycycline and rifampin; N-methyl-D-aspartate (NMDA) receptor antagonists, such as memantine, neramexane and EVT101; NR2B antagonists; androgen receptor modulators; acetylcholinesterase inhibitors such as galantamine, rivastigmine, donepezil, tacrine, phenserine, ladostigil and ABT-089; mGluR5 modulators; growth hormone secretagogues such as ibutamoren, ibutamoren mesylate, and capromorelin; histamine $H_3$ receptor antagonists, such as ABT834, ABT239, GSK 189254 and CEP16795; AMPA agonists or AMPA modulators, such as CX717, LY404187 and S-18986; PDE IV inhibitors, such as MEM141, HT0712 and AVE8112; $GABA_A$ inverse agonists; $GABA_A$ α5 receptor ligands; $GABA_B$ receptor ligands; potassium channel blockers; neuronal nicotinic agonists, such as ABT089; plasminogen activator inhibitors, such as PAZ417; cathepsin B inhibitors; GSK3β inhibitors, such as AZD1080, SAR502250 and CEP 16805; selective M1 agonists; neuronal nicotinic agonists, microtubule affinity regulating kinase (MARK) ligands; P450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention and includes (1) inhibiting the disease in an animal that is experiencing or displaying the pathology or symptomotology of the diseased (i.e., arresting further development of the pathology and/or symptomotology), or (2) ameliorating the disease in an animal that is experiencing or displaying the pathology or symptomotology of the diseased (i.e., reversing the pathology and/or symptomotology). The term "controlling" includes preventing treating, eradicating, ameliorating or otherwise reducing the severity of the condition being controlled.

The compositions containing compounds of the invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition may be determined as follows.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 mL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared, and the concentration rage is dependent on the potency predicted by ECL. Solutions of inhibitor in DMSO are included in the reaction mixture (final DMSO concentration is 10%). All experiments are conducted at rt using the standard reaction conditions described above. To determine the $IC_{50}$ of the compound, four parameters equation is used for curve fitting. The errors in reproducing the dissociation constants are typically less than two-fold.

ECL Assay: A homogeneous end point electrochemiluminescence (ECL) assay is performed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 μM with three fold series dilution. Solutions of the inhibitor in DMSO are included in the reaction mixture (final DMSO concentration is 10%). All experiments are conducted at rt using the standard reaction conditions described above. To determine the IC$_{50}$ of the compound, a four parameter equation is used for curve fitting. The errors in reproducing the dissociation constants are typically less than two-fold.

In particular, the compounds of the following examples had activity in inhibiting the beta-secretase enzyme in the ECL assay, generally with an IC$_{50}$ from about 1 nM to 100 μM. Such a result is indicative of the intrinsic activity of the compounds as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate I Tert-Butyl (3-benzyl-2-hydroxytetrahydrofuran-3-yl)carbamate: (Scheme 1)

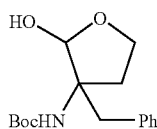

Step A: Schiff Base Installation

To a solution of 3-aminodihydrofuran-2(3H)-one hydrobromide (5 g, 27.5 mmol) in DCM (50 mL) was added benzophenone imine (5 g, 27.5 mmol) and the reaction mixture was stirred at RT for 3 days. The reaction mixture was diluted with water and DCM, the organic layer was extracted, washed with aquous sodium bicarbonate, brine, dried over sodium sulfate and concentrated in vacuo to give 3-[(diphenylmethylene)amino]dihydrofuran-2(3H)-one as a thick colorless gel which crystallized to a white solid.

Step B: Alkylation

To a solution of 3-[(diphenylmethylene)amino]dihydrofuran-2(3H)-one (1 g, 3.8 mmol) in DMF (10 mL) cooled to 0° C. was added NaHMDS (4.7 mL, 4.7 mmol, 1M THF) via serynge slowly. The resulting bright orange solution was stirred at 0° C. for 2 min at which point benzyl bromide (0.47 mL, 4 mmol) was addedvia serynge. After 5 min stirring at 0° C., the reaction was quenched with water, extracted with EtOAc, washed with aqueous LiCl, dried over sodium sulfate, concentrated in vacuo, and purified by flash chromatography (90 g silica gel, 0 to 40% EtOAc in hexane) to give 3-benzyl-3-[(diphenylmethylene)amino]dihydrofuran-2(3H)-one as a white solid. MS M+1=356.

Step C: Hydrolysis

To a solution of 3-benzyl-3-[(diphenylmethylene)amino] dihydrofuran-2(3H)-one (5.67 g, 15.95 mmol) in MeOH (50 mL) and THF (50 mL) was added 6N HCl (5.3 mL, 32 mmol). After 5 min stirring at RT, the reaction mixture was concentrated in vacuo, diluted with water and benzophenone was extracted with diethyl ether (3x). The aqueous layer was basified to pH 10 with 6N NaOH, extracted with DCM (x2), dried over sodium sulfate and concentrated in vacuo to give 3-amino-3-benzyldihydrofuran-2(3H)-one as a colorless oil, which was carried as is in the next step.

Step D: Boc Installation

To a solution of 3-amino-3-benzyldihydrofuran-2(3H)-one (2.55 g, 13.3 mmol) in THF (25 mL) was added ditertbutyl dicarbonate (3.2 g, 14.7 mmol). The reaction mixture was concentrated in vacuo to afford crude tert-butyl (3-benzyl-2-oxotetrahydrofuran-3-yl)carbamate as a white solid. MS M+Na=314

Step E: Reduction

To a solution of tert-butyl (3-benzyl-2-oxotetrahydrofuran-3-yl)carbamate (4.18 g, 14.3 mmol) in THF (100 mL) cooled to −78° C. was added DIBAL-H (57.4 mL, 57.4 mL, 1M hexane) dropwise over 15 min. The reaction mixture was stirred at −78° C. for 5 h, quenched with EtOAc, diluted with diethyl ether and aqueous Rochelle's salt. Vigorous stirring was allowed until gel break-up and layer formation. The organic layer was extracted, washed with aqueous Rochelle's salt, water, brine, dried over sodium sulfate, concentrated in vacuo, and purified by flash chromatography (120 g silica gel, 0 to 40% EtOAc in hexane) to give tert-butyl (3-benzyl-2-hydroxytetrahydrofuran-3-yl)carbamate (intermediate I) as a white foam (ca. 1:1 diastereomeric ratio). $^1$H NMR (400 MHz, CDCl$_3$) δ 7.35-7.12 (m, 5H), 5.35 (s, 0.5H), 5.32 (s, 0.5H), 5.97 (s, 0.5H), 4.25 (s, 0.5H), 4.20-4.08 (m, 1H), 4.00-3.86 (m, 1H), 3.48-2.88 (m, 3H), 2.28-1.84 (m, 2H), 1.49 (s, 4.5H), 1.47 (s, 4.5H). MS M+Na=316.

Intermediate A Methyl 3-(hydroxymethyl)-5-[(methylsulfonyl)(propyl)amino]benzoate: (Scheme 2)

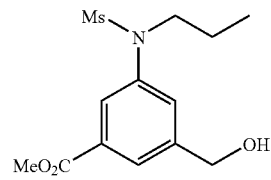

Intermediate A was prepared following the procedure described in WO 2005/032471, intermediate A: Step A (sulfonylation with mesyl chloride), Step B (alkylation with propyl iodide), Step C (mono-hydrolysis), Step E (reduction with borane).

Intermediate B Methyl 2'-cyano-5 (hydroxymethyl)biphenyl-3-carboxylate: (Scheme 3)

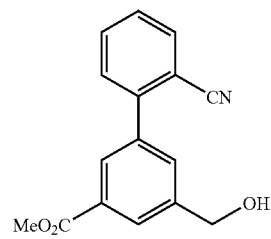

Intermediate B was prepared following the procedure described in WO 2005/032471, intermediate B, omitting the final bromination.

Intermediate C N-[6-chloro-4 hydroxymethyl)pyridin-2-yl]-N-propylmethanesulfonamide: (Scheme 4)

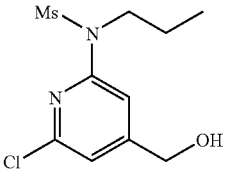

Step A: Sulfonamide Installation

A solution of methyl 2,6-dichloroisonicotinate (4.8 g, 23.3 mmol) and N-propylmethanesulfonamide (3.8 g, 28.0 mmol) in dioxane (190 mL) was degassed with argon. Potassium phosphate tribasic (6.9 g, 32.6 mmol), xantphos (810 mg, 1.40 mmol) and $Pd_2$ $dba_3$ (427 mg, 0.47 mmol) were added, and the reaction mixture was stirred at 100° C., sealed, for 16 h. The reaction mixture was filtered on cellite, concentrated in vacuo, and purified by flash chromatography (2×300 g silica gel, 0 to 35% EtOAc in hexane) to give methyl 2-chloro-6-[(methylsulfonyl)(propyl)amino]isonicotinate. $^1H$ NMR (400 MHz, $CD_3OD$) δ 7.87 (s, 1H), 7.72 (s, 1H), 3.97 (s, 3H), 3.91 (t, J=7.2 Hz, 2H), 3.14 (s, 3H), 1.68-1.52 (m, 2H), 0.94 (t, J=7.4 Hz, 3H).

Step B: Reduction

To a solution of methyl 2-chloro-6-[(methylsulfonyl)(propyl)amino]isonicotinate (3.52 g, 11.47 mmol) in THF (50 mL), cooled to 0° C., was added lithium borohydride (17.3 mL, 34.4 mmol, 2M THF) slowly via serynge. The reaction mixture was allowed to warm to RT by itself and stirred at RT for 3 h. The reaction mixture was carefully quenched with EtOAc, MeOH and water sequentially. The reaction mixture was diluted with EtOAc, the organic layer was separated, dried over sodium sulfate and concentrated in vacuo to give N-[6-chloro-4(hydroxymethyl)pyridin-2-yl]-N-propylmethanesulfonamide as a yellow thick oil. $^1H$ NMR (400 MHz, $CDCl_3$) δ 7.27 (s, 1H), 7.23 (s, 1H), 4.72 (s, 2H), 3.80 (t, J=8 Hz, 2H), 3.00 (s, 3H), 2.02 (s, 1H), 1.59-1.46 (m, 2H), 0.90 (t, J=7.6 Hz, 3H).

EXAMPLE 1

3-{[(3-amino-3-benzyltetrahydrofuran-2-yl)oxy]methyl}-N-[(1R)-1-(4-fluorophenyl)ethyl]-5-[(methylsulfonyl)(propyl)amino]benzamide (scheme 5

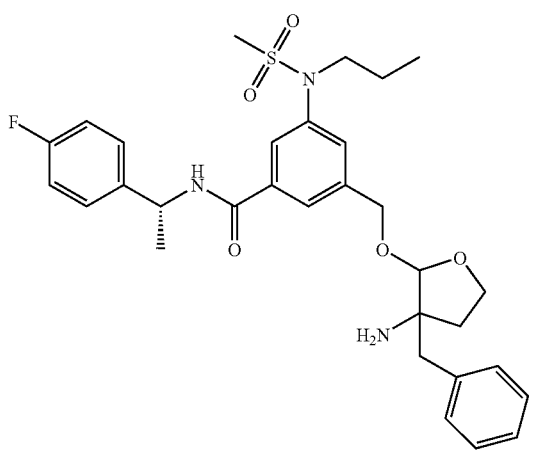

Step A: Glycosylation/Boc Removal

To a solution of tert-butyl (3-benzyl-2-hydroxytetrahydrofuran-3-yl)carbamate (50 mg, 0.17 mmol, intermediate I and methyl 3-(hydroxymethyl)-5-[(methylsulfonyl)(propyl) amino]benzoate (62 mg, 0.21 mmol, intermediate A in toluene (0.6 mL) was added a catalytic amount of pTsA and the reaction mixture was stirred at 160° C., sealed, for 4 h. The reaction mixture was purified by ion exchange chromatography (Varian SCX, MeOH then $NH_3$/MeOH) and then purified by preparative HPLC (5->95% $CH_3CN/H_2O$, 0.1% added TFA, C18 Sunfire Waters, 30×150 mm) to give methyl 3-{[(3-amino-3-benzyltetrahydrofuran-2-yl)oxy]methyl}-5-[(methylsulfonyl)propyl)amino]benzoate as a white solid (TFA salt). 1:1 diastereomeric mixture. MS M+1=477.

Step B: Hydrolysis

To a solution of methyl 3-{[(3-amino-3-benzyltetrahydrofuran-2-yl)oxy]methyl}-5-[(methylsulfonyl)(propyl)amino] benzoate TFA salt (40 mg, 0.07 mmol) in THF (0.5 mL) and MeOH (0.5 mL) is 1N LiOH (0.6 mL, 0.6 mmol) and the reaction mixture is stirred at RT for 3 h. 1N HCl (0.4 mL, 0.4 mmol) is added and the reaction mixture is concentrated in vacuo to give 3-{[(3-amino-3-benzyltetrahydrofuran-2-yl)oxy]methyl}-5-[(methylsulfonyl)(propyl)amino]benzoic acid as a white solid, used as is in the following coupling.

Step C: Coupling

A solution of 3-{[(3-amino-3-benzyltetrahydrofuran-2-yl)oxy]methyl}-5-[(methylsulfonyl)(propyl)amino]benzoic acid (25 mg, 0.04 mmol), 4-fluoro-R-alpha-methyl-benzyl amine (10 mg, 0.08 mmol), N,N-diisopropylethylamine (0.02 mL, 0.11 mmol), BOP reagent (25 mg, 0.06 mmol) in DMF (0.6 mL) is stirred at RT for 20 min and purified by preparative HPLC (5->95% $CH_3CN/H_2O$, 0.1% added TFA, C18 Sunfire Waters, 30×150 mm) to give 3-{[(3-amino-3-benzyltetrahydrofuran-2-yl)oxy]methyl}-N-[(1R)-1-(4-fluorophenyl) ethyl]-5-[(methylsulfonyl)(propyl)amino]benzamide (2 diastereoisomer separated). MS M+1=584.

EXAMPLE 2

3'-{[(3-amino-3-benzyltetrahydrofuran-2-yl)oxy]methyl}-5'-{[(2R)-2R)-2-prop-1-yn-1-ylpyrrolidin-1-yl]carbonyl}biphenyl-2-carbonitrile (Scheme 6)

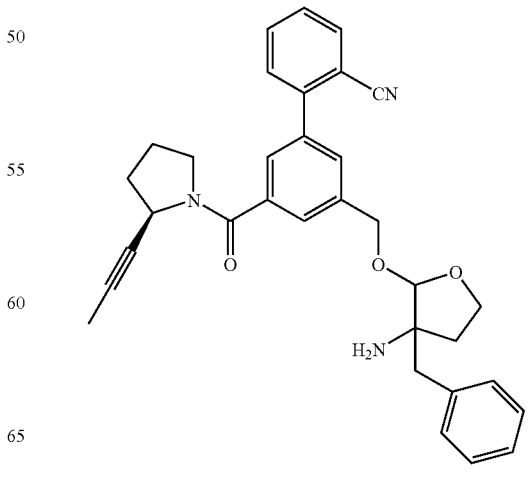

3'-{[(3-amino-3-benzyltetrahydrofuran-2-yl)oxy]methyl}-5'-{[(2R)-2-prop-1-yn-1-ylpyrrolidin-1-yl]carbonyl}biphenyl-2-carbonitrile was prepared from the coupling of intermediates I and B (step A), followed by hydrolysis (step B) and coupling with (2R)-2-prop-1-yn-1-ylpyrrolidine (step C), following a similar procedure as described in example 1. MS M+1=520.

EXAMPLE 3

N-[4-{[(3-amino-3-benzyltetrahydrofuran-2-yl)oxy]methyl}-6-((2-methoxyethyl){[(1S,2S)-2-methylcyclopropyl]methyl}amino)pyridin-2-yl]-N-propyl-methanesulfonamide (Scheme 7)

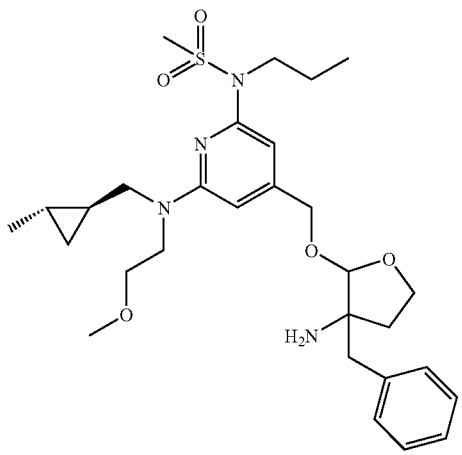

Step A: Glycosylation/Boc Removal

To a solution of tert-butyl (3-benzyl-2-hydroxytetrahydrofuran-3-yl)carbamate (500 mg, 1.70 mmol, intermediate I and N-[6-chloro-4(hydroxymethyl)pyridin-2-yl]-N-propyl-methanesulfonamide (451 mg, 1.62 mmol, intermediate C in toluene (3 mL) was added a catalytic amount of pTsA and the reaction mixture was stirred at 160° C., sealed, for 4.5 h Additional intermediate A (150 mg) was added and the reaction mixture was stirred at 160° C., sealed, for 20 h. The reaction mixture was concentrated in vacuo and crude N-4-{[(3-amino-3-benzyltetrahydrofuran-2-yl)oxy]methyl}-6-chloropyridin-2-yl)-N-propylmethanesulfonamide was used as is in the next step. MS M+1=454.

Step B: Boc Installation

To a solution of crude N-(4-{[(3-amino-3-benzyltetrahydrofuran-2-yl)oxy]methyl}-6-chloropyridin-2-yl)-N-propyl-methanesulfonamide (800 mg, 1.76 mmol) in THF (10 mL) was added diisopropylethyl amine (1.53 mL, 8.8 mmol) and ditertbutyl dicarbonate (770 mg, 3.52 mmol), and the reaction mixture was stirred at 60° C. for 16 h. The reaction mixture was concentrated in vacuo, and purified by flash chromatography (120 g silica gel, 0 to 35% EtOAc in hexane) to give tert-butyl[3-benzyl-2-({2-chloro-6-[(methylsulfonyl)(propyl)amino]pyridin-4-yl}methoxy)tetrahydrofuran-3-yl]carbamate as a brown foam. MS M+1=554.

Step C: Amination

A solution of tert-butyl[3-benzyl-2-{2-chloro-6-[(methylsulfonyl)(propyl)amino]pyridin-4-yl}methoxy)tetrahydrofuran-3-yl]carbamate (270 mg, 0.49 mmol) and (2-methoxyethyl){[(1S,2S)-2-methylcyclopropyl]methyl}amine (174 mg, 1.22 mmol, prepared as described in commonly owned International patent application no. PCT/US2005/013480, filed Apr. 20, 2005) in DMA (5 mL) was degassed with argon for 10 min. Potassium phosphate tribasic (310 mg, 1.46 mmol), di-tritertbutylphosphine palladium (25 mg, 0.05 mmol) were added and the reaction mixture was stirred, sealed under argon, at 120° C. for 40 min. The reaction mixture was diluted with water, extracted with EtOAc, washed with aqueous lithium chloride (×3), dried over sodium sulfate, concentrated in vacuo, and purified by flash chromatography (40 g silica gel, 0 to 40% EtOAc in hexane) to give tert-butyl[3-benzyl-2-({2-(2-methoxyethyl){[(1S,2S)-2-methylcyclopropyl]methyl}amino)-6-[(methylsulfonyl)(propyl)amino]pyridin-4-yl}methoxy)tetrahydrofuran-3-yl]carbamate as a yellow foam MS M+1=661.

Step D: Boc Removal tert-butyl[3-benzyl-2-({2(2-methoxyethyl){[(1S,2S)-2-methylcyclopropyl]methyl}amino)-[(methylsulfonyl)(propyl)amino]pyridin-4-yl}methoxy)tetrahydrofuran-3-yl]carbamate (180 mg, 0.27 mmol) was treated with TFA (2 mL) in DCM (2 mL) for 1 h 30. The reaction mixture was purified by preparative HPLC (5->95% CH$_3$CN/H$_2$O, 0.1% added TFA, C18 Sunfire Waters, 30×150 mm) to give N-[4-{[(3-amino-3-benzyltetrahydrofuran-2-yl)oxy]methyl}-6-((2-methoxyethyl) {[(1S,2S)-2-methylcyclopropyl]methyl}amino)pyridin-2-yl]-N-propylmethanesulfonamide. MS M+1=561.

The following abbreviations are used throughout the text:
Me: methyl
Et: ethyl
t-Bu: tert-butyl
Ar: aryl
Ph: phenyl
Bn: benzyl
Ac: acetyl
DMF: N,N'-dimethyl formamide
HMDS: hexamethyldisilazane
THF: tetrahydrofuran
DIBAL: diisobutylaluminum hydride
BOP: Benzotriazol-1-yloxy-tris(dimethylamino)phosphonium hexafluorophosphate
TMS: trimethylsilyl
pTsA: para toluene sulfonic acid
DCM: methylene chloride
EDC: 1-Ethyl-3-(3-dimethylaminopropyl)-carbodiimide
HOAt: 1-Hydroxy-7-azabenzotriazole
DMSO: dimethylsulfoxide
EDTA: ethylene diamine tetraacetic acid
Boc: tert-butyloxy carbonyl
CHAPS: 3-[(3-cholamidopropyl)dimethylammonio]-2-hydroxy-1-propanesulfonate
BSA: bovine serum albumin
TFA: trifluoracetic acid
rt: room temperature
aq: aqueous
HPLC: high performance liquid chromatography
Ms: mesyl
MS: mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

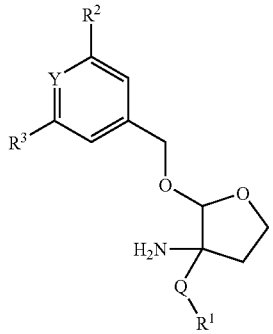

(I)

wherein

Y is N or CH;

Q is —$C_{0-3}$ alkylene, wherein said alkylene is unsubstituted or substituted with one or more
(1) halo,
(2) —$C_{3-12}$ cycloalkyl,
(3) —OH,
(4) —CN,
(5) —O—$C_{1-10}$ alkyl, and
(6) —$C_{1-10}$ alkyl;

$R^1$ is (1) aryl selected from the group consisting of phenyl and napthyl,
(2) heteroaryl,
(3) —$C_{1-10}$ alkyl, and
(4) —$C_{3-8}$ cycloalkyl, said cycloalkyl optionally fused to a $C_{6-10}$ aryl group,
wherein said alkyl, cycloalkyl, aryl or heteroaryl is unsubstituted or substituted with one or more
(a) halo,
(b) —$C_{1-10}$ alkyl, wherein said alkyl is unsubstituted or substituted with halogen,
(c) —OH,
(d) —CN,
(e) —O—$C_{1-10}$ alkyl,
(f) —$C_{3-12}$ cycloalkyl, and
(g) —$NR^{12}R^{13}$, wherein $R^{12}$ and $R^{13}$ are selected from the group consisting of
(i) hydrogen,
(ii) —$C_{1-10}$ alkyl, and
(iii) —$C_{0-6}$ alkyl-$C_{6-10}$ aryl;

$R^2$ is selected from the group consisting of:
(1) ($R^4$—$SO_2$)N($R^7$)—, wherein $R^4$ is
(a) —$C_{1-10}$ alkyl,
(b) —$C_{2-10}$ alkenyl,
(c) —$C_{2-10}$ alkynyl, or
(d) —$C_{3-8}$ cycloalkyl,
wherein said alkyl, alkenyl, alkynyl and cycloalkyl is unsubstituted or substituted with one or more
(i) halo,
(ii) —OH,
(iii) —CN,
(iv) —O—$C_{1-10}$ alkyl,
(v) —$C_{1-10}$ alkyl,
(vi) —$C_{2-10}$ alkenyl,
(vii) —$C_{2-10}$ alkynyl,
(viii) —$C_{3-8}$ cycloalkyl,
(ix) aryl selected from the group consisting of phenyl and napthyl, or
(x) heteroaryl,
and said aryl and heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) —$C_{1-10}$ alkyl,
(vii) —$C_{2-10}$ alkenyl, or
(viii) —$C_{2-10}$ alkynyl;

$R^7$ is selected from the group consisting of
(a) hydrogen,
(b) —$C_{1-10}$ alkyl,
(c) —$C_{2-10}$ alkenyl, or
(d) —$C_{2-10}$ alkynyl,
wherein said alkyl, alkenyl or alkynyl is unsubstituted or substituted with one or more
(i) halo,
(ii) —OH,
(iii) —CN,
(iv) —O—$C_{1-10}$ alkyl,
(v) —$C_{3-8}$ cycloalkyl,
(vi) aryl selected from the group consisting of phenyl and napthyl, or
(vii) heteroaryl,
and said cycloalkyl, aryl or heteroaryl is unsubstituted or substituted with one or more
(i) halo,
(ii) —OH,
(iii) —CN,
(iv) —O—$C_{1-10}$ alkyl,
(v) —$C_{3-8}$ cycloalkyl, or
(vi) aryl selected from the group consisting of phenyl and napthyl;

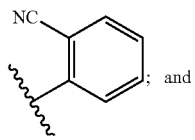

(2)

and

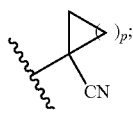

(3)

$R^3$ is selected from the group consisting of

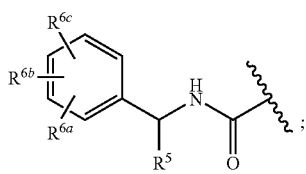

(1)

-continued

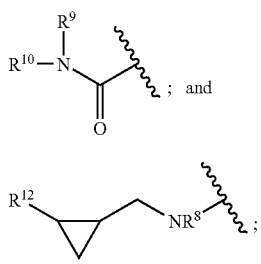

(2)

(3)

wherein $R^5$ is selected from the group consisting of
(1) —$C_{1-10}$ alkyl,
(2) —$C_{2-10}$ alkenyl, or
(3) —$C_{2-10}$ alkynyl,
wherein said alkyl, alkenyl or alkynyl is unsubstituted or is substituted with one or more halo;
$R^{6a}$, $R^{6b}$, and $R^{6c}$ are independently selected from the group consisting of:
(1) hydrogen,
(2) halo,
(3) —$C_{1-10}$ alkyl,
(4) —$C_{2-10}$ alkenyl,
(5) —$C_{2-10}$ alkynyl,
(6) —OH,
(7) —CN,
(8) —$C_{3-8}$ cycloalkyl, and
(9) —O—$C_{1-10}$ alkyl;
$R^9$ and $R^{10}$ are independently selected from the group consisting of
(1) hydrogen,
(2) —$C_{1-10}$ alkyl,
(3) —$C_{2-10}$ alkenyl,
(4) —$C_{2-10}$ alkynyl, or
(5) —$C_{3-8}$ cycloalkyl;
wherein said alkyl, alkenyl, alkynyl or cycloalkyl is unsubstituted or substituted with one or more
(a) halo,
(b) —OH,
(c) —CN,
(d) —$C_{3-8}$ cycloalkyl, or
(e) —O—$C_{1-10}$ alkyl,
or $R^9$ and $R^{10}$ are joined together with the nitrogen atom to which they are attached to form a pyrrolidine ring, which is unsubstituted or substituted with one or more
(a) $C_{1-10}$ alkyl,
(b) —$C_{2-10}$ alkenyl,
(c) —$C_{2-10}$ alkynyl,
(d) —$C_{3-8}$ cycloalkyl,
(e) —$(CH_2)_n$-phenyl,
(f) —CN,
wherein said alkyl, alkenyl or alkynyl is unsubstituted or substituted with one or more
(i) halo,
(ii) —OH,
(iii) —CN,
(iv) —O—$C_{1-10}$ alkyl, or
(v) —$C_{3-8}$ cycloalkyl,
and said cycloalkyl and phenyl is unsubstituted or substituted with one or more
(i) halo,
(ii) —$C_{1-10}$ alkyl,
(iii) —$C_{2-10}$ alkenyl,
(iv) —$C_{2-10}$ alkynyl,
(v) —OH,
(vi) —CN,
(vii) —$C_{3-8}$ cycloalkyl, or
(viii) —O—$C_{1-10}$ alkyl;
$R^8$ is selected from the group consisting of
(1) hydrogen,
(2) —$C_{1-10}$ alkyl,
(3) —$C_{2-10}$ alkenyl,
(4) —$C_{2-10}$ alkynyl, or
(5) —$CH_{2-10}$ phenyl,
wherein said alkyl, alkenyl, alkynyl or phenyl is unsubstituted or substituted with one or more
(a) halo,
(b) —OH,
(c) —CN,
(d) —$C_{3-8}$ cycloalkyl, and
(e) —O—$C_{1-10}$ alkyl;
$R^{12}$ is selected from the group consisting of
(1) hydrogen,
(2) —$C_{1-10}$ alkyl,
(3) —$C_{2-10}$ alkenyl,
(4) —$C_{2-10}$ alkynyl,
(5) halo,
(6) —$C_{3-8}$ cycloalkyl,
(7) aryl selected from the group consisting of phenyl and napthyl, and
(8) heteroaryl,
wherein said aryl and heteroaryl is unsubstituted or substituted with one or more
(a) halo,
(b) —OH,
(c) —CN,
(d) —O—$C_{1-10}$ alkyl,
(e) —$C_{3-8}$ cycloalkyl,
(f) —$C_{1-10}$ alkyl,
(g) —$C_{2-10}$ alkenyl, or
(h) —$C_{2-10}$ alkynyl
n is 0, 1, 2, 3 or 4;
p is 1, 2, 3 or 4;
and pharmaceutically acceptable salts thereof, and individual enantiomers and diastereomers thereof.

2. A compound of claim 1, wherein $R^1$ is phenyl and Q is $CH_2$.

3. A compound of claim 1, wherein $R^1$ is 4-fluorophenyl and Q is $CH_2$.

4. A compound of claim 1, wherein $R^1$ is heteroaryl selected from the group consisting of pyridyl, thienyl, thiazole and indynyl.

5. A compound of claim 1, wherein $R^1$ is $C_{1-12}$ alkyl or $C_{3-8}$ cycloalkyl.

6. A compound of claim 1, wherein $R^2$ is selected from the group consisting of
(1) $(R^4—SO_2)N(R^7)$—, wherein $R^4$ is —$C_{1-6}$ alkyl, wherein said alkyl is unsubstituted or substituted with one or more
(i) halo,
(ii) —OH,
(iii) —CN,
(iv) —O—$C_{1-6}$ alkyl, or
(v) —$C_{1-6}$ alkyl,
$R^7$ is selected from the group consisting of
(a) hydrogen,
(b) —$C_{1-6}$ alkyl,
wherein said alkyl is unsubstituted or substituted with one or more
(i) halo,
(ii) —OH, (iii) —CN,
(iv) —O—$C_{1-6}$ alkyl,
(v) —$C_{1-6}$ alkyl,

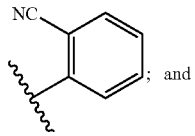
(2)

; and

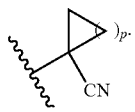
(3)

7. A compound of claim 1, wherein $R^3$ is selected from the group consisting of

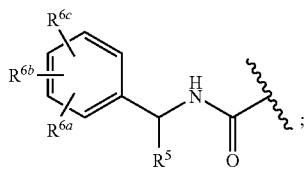
(a)

;

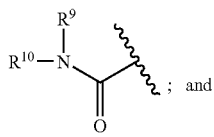
(b)

; and

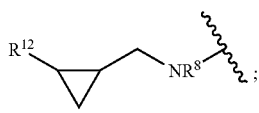
(c)

;

wherein $R^5$ is $C_{1-6}$ alkyl, optionally substituted with one or more halogen (preferably fluoro);
$R^{6a}$, $R^{6b}$, and $R^{6c}$ are independently selected from the group consisting of:
(1) hydrogen,
(2) halo,
(3) —$C_{1-6}$ alkyl,
(4) —OH,
(5) —CN, and
(6) —O—$C_{1-6}$ alkyl;
$R^9$ and $R^{10}$ are independently selected from the group consisting of
(1) hydrogen, and
(2) —$C_{1-6}$ alkyl,
or $R^9$ and $R^{10}$ are joined together with the nitrogen atom to which they are attached to form a pyrrolidine ring, which is unsubstituted or substituted with one or more
(a) $C_{1-6}$ alkyl,
(b) —$(CH_2)_n$-phenyl;
wherein said alkyl and phenyl is unsubstituted or substituted with one or more
(i) halo,
(ii) —$C_{1-6}$alkyl,
(iii) —OH,
(iv) —CN, or
(v) —O—$C_{1-6}$ alkyl; and
$R^{12}$ is selected from the group consisting of
(1) hydrogen,
(2) —$C_{1-6}$ alkyl.

8. A compound of claim 7, wherein $R^3$ is

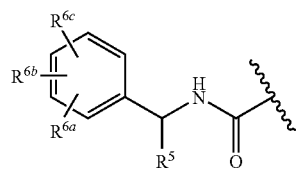
(a)

wherein $R^5$, $R^{6a}$, $R^{6b}$, $R^{6c}$ are as defined above. In preferred embodiments, $R^5$ is $C_{1-6}$ alkyl, optionally substituted with one or more halogen (preferably fluoro); and $R^{6a}$, $R^{6b}$, and $R^{6c}$ are independently selected from the group consisting of:
(1) hydrogen,
(2) halo,
(3) —$C_{1-6}$alkyl,
(4) —OH,
(5) —CN, and
(6) —$C_{1-6}$alkyl.

9. A compound of claim 8, wherein $R^5$ is methyl, $R^{6a}$ and $R^{6b}$ are hydrogen and $R^{6c}$ is fluoro.

10. A compound of claim 1, wherein Y is CH.

11. A compound of claim 1, wherein Y is N.

12. A compound of claim 1, which is a compound of formula (II)

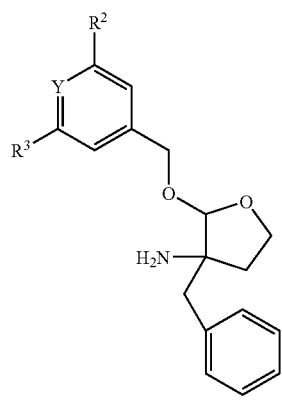
(II)

wherein $R^2$, $R^3$ and Y are as defined in claim 1, and pharmaceutically acceptable salts thereof, and individual enantiomers and diastereomers thereof.

13. A compound of claim 1, which is selected from the group consisting of

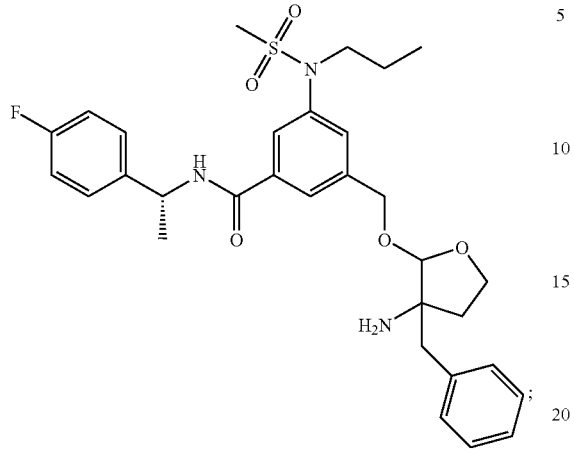

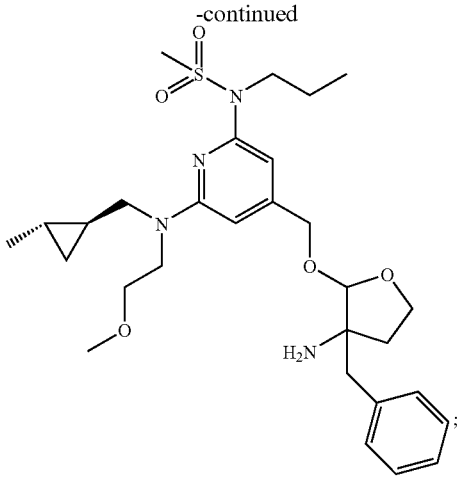

and pharmaceutically acceptable salts thereof.

14. A pharmaceutical composition comprising a therapeutically effective amount of a compound of claim 1 and a pharmaceutically acceptable carrier.

15. A method for inhibiting BACE1 enzyme activity in a mammal in need thereof which comprises administering to the mammal a therapeutically effective amount of a compound of claim 1.

16. A method for inhibiting BACE2 enzyme activity in a mammal in need thereof which comprises administering to the mammal a therapeutically effective amount of a compound of claim 1.

17. A method for treating Alzheimer's disease in a patient in need thereof comprising administering to the patient a therapeutically effective amount of a compound of claim 1.

* * * * *